United States Patent [19]

Kubushiro

[11] 4,052,282

[45] Oct. 4, 1977

[54] PHOTOCURABLE FLEXIBLE ORTHOPEDIC BANDAGE

[75] Inventor: Kanemitsu Kubushiro, Ami, Japan

[73] Assignee: Mitsubishi Petrochemical Co., Ltd., Tokyo, Japan

[21] Appl. No.: 620,844

[22] Filed: Oct. 8, 1975

[51] Int. Cl.² ............................ C08F 2/46; C08F 4/00
[52] U.S. Cl. .................... 204/159.23; 204/159.12; 204/159.15; 204/159.19; 204/159.22; 128/90; 260/8; 260/17.4 GC; 260/42.18; 260/42.53; 260/859 R; 428/268; 428/273; 428/425
[58] Field of Search .................. 204/159.22, 159.19, 204/159.16, 159.23, 159.12, 159.15; 128/90

[56] References Cited

U.S. PATENT DOCUMENTS

| | | | |
|---|---|---|---|
| 3,297,745 | 1/1967 | Fekete et al. | 260/471 |
| 3,694,415 | 9/1972 | Honda et al. | 260/77.5 CR |
| 3,719,638 | 3/1973 | Huemmer et al. | 260/77.5 CR |
| 3,862,920 | 1/1975 | Foster et al. | 260/42.52 |
| 3,874,376 | 4/1975 | Dort et al. | 128/90 |
| 3,881,473 | 5/1975 | Corvi et al. | 128/90 |

*Primary Examiner*—Richard B. Turer
*Attorney, Agent, or Firm*—Sherman & Shalloway

[57] ABSTRACT

A photocurable bandage or splint consisting of a flexible fabric, a photosensitizer and a reaction product of a hydroxyalkyl acrylate or methacrylate, a diisocyanate and a polyhydric alcohol. The photocurable bandage or splint can be produced without using a solvent and a volatile monomer by using a process which comprises impregnating the flexible fabric with a reaction mixture obtained by adding the polyhydric alcohol to a reaction product of the hydroxyalkyl acrylate or methacrylate and the diisocyanate which contains free isocyanate groups, and reacting the polyhydric alcohol with the isocyanate groups on the fabric to form a photocurable composition.

17 Claims, No Drawings

PHOTOCURABLE FLEXIBLE ORTHOPEDIC BANDAGE

This invention relates to a photocurable flexible orthopedic material such as bandage or splint, and a method for producing it.

Orthopedic bandages composed of calcined gypsum and a fibrous base material such as gauze have been used from old to cover or fix members of a body, for example, in the treatment of bone fracture. These bandages, however, have the defect of heavy weight, insufficient strength, poor water resistance and impermeability to X rays.

U.S. Pat. No. 3,089,486 discloses an improvement of such a bandage containing gypsum. This bandage, however, suffers from various disadvantages. For example, because of using a curable low-boiling methacrylate monomer, it gives off an unpleasant odor. It has poor storage stability, and therefore, must be used immediately upon impregnation. Also, the curing of the monomer is time-consuming.

In an attempt to make further improvement, therefore, photocurable orthopedic bandages using an ultraviolet curable polymer have recently been developed. U.S. Pat. No. 3,421,501 suggests an orthopedic bandage produced by impregnating a glass fiber cloth or fabric with a photocurable unsaturated polyester. The unsaturated polyester, however, essentially requires the addition of a cross-linking monomer compatible with it, such as sytrene, methyl styrene or methyl methacrylate. Since such a monomer to be added to the unsaturated polyester is mainly a low-boiling compound, it is very liable to volatilize off before the completion of curing. Thus, when the bandage is used to dress wounds, it gives off a very unpleasant odor. Furthermore, styrene or the like monomer is known to have an irritating action, and exhibit a medium degree of toxicity (transitory irritation) toward skins, eyes and mucous membranes [N. Irving Sax, "Dangerous Properties of Industrial Materials", Vol. 2, page 1090, 1963]. Because of such a toxicity, the volatilization of a vapor of such a monomer is undesirable both to patients and persons who dress them with bandages. Moreover, since the volatilization of such a monomer causes a change in the composition of the bandage impregnated with the unsaturated polyester resin, the storage stability of the bandage after unsealing is poor, and when the bandage is stored for long periods of time after unsealing, it canot retain sufficient strength.

Furthermore, since the unsaturated polyester resin itself which is suited for bandages has an extremely high viscosity, and is difficult to impregnate directly in a base material such as a fibrous material, it is necessary to dilute the polyester resin with a suitable solvent before impregnation, and after impregnation, remove the solvent. It is extremely difficult to remove only the solvent without removing the volatile monomer added to the unsaturated polyester. In this regard, too, the chemical composition of the resin is difficult to maintain constant. The U.S. Pat. No. 3,421,501 also suggests the use of trially cyanurate, a high-boiling monomer, instead of the volatile monomer. But this monomer presents difficulties in actual application because it is irritating to the skin and has poor photocurability.

Because the unsaturated polyester of such a bandage is cured while the bandage is being applied to a member of a body, it cannot be cured by heating, but is cured substantially at room temperature. Thus, the odor of the monomer such as styrene does not go off even after curing, and the patient is compelled to smell the bad smell for long periods of time. This is inconvenient in actual application of such a bandage.

Accordingly, an object of this invention is to provide a photocurable flexible orthopedic material such as a bandage or splint to be applied to members of a body, which comprises a flexible fabric, a photosensitizer and a photocurable flexible composition free from volatile monomer and a solvent and has storage stability, and a method for producing the flexible orthopedic material.

Another object of this invention is to provide a composition which can be impregnated easily in a fabric without using a volatile monomer, and can give a photopolymerizable and photocurable tacky composition.

The present invention provides a storage-stable flexible photocurable orthopedic material such as a bandage or splint for application to a body member, said orthopedic material comprising a flexible fabric, a photosensitizer and a photocurable tacky composition impregnated in the fabric, said tacky composition being a reaction product obtained by reacting a reaction product (D) of A. at least one hydroxyalkyl acrylate or hydroxyalkyl methacrylate, wherein said hydroxyalkyl portion contains 2 or 3 carbon atoms and B. 0.55 to 3 moles, per mole of the acrylate, of at least one diisocyanate of the following formula

OCN—R$_1$—NCO wherein R$_1$ represents 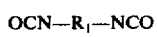

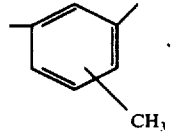

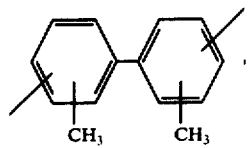

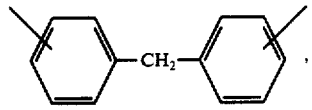

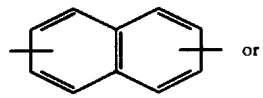

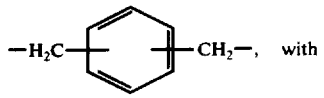, with

C. at least one polyhydric alcohol of the following formula

R$_2$(OH)$_m$ wherein R$_2$ represents a straight-chain or branched chain saturated aliphatic hydrocarbon group containing 2 to 8 carbon atoms, a cycloaliphatic hydrocarbon group, or the group

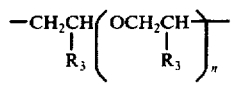

in which $n$ is a number of 1 to 4 and $R_3$ is a hydrogen atom methyl groups and $m$ is 2 or 3,
said reaction product of (D) and (C) containing at least one compound containing at least two carbon-carbon double bonds capable of being polymerized and crosslinked by light and being substantially free from isocyanate group.

The characteristic feature of the orthopedic material such as a bandage or splint to be applied to a body member is that the photocurable tacky composition impregnated in the fabric consists of a reaction product of components (A), (B) and (C).

The tacky photocurable composition used in this invention differs from a known composition comprising a high viscosity unsaturated polyester and a low viscosity crosslinking agent such as styrene and capable of being crosslinked by irradiation of ultraviolet rays, and comprises compounds of a relatively low molecular weight. It is cured as a result of the polymerization and crosslinking of at least two functional groups (i.e., acrylate groups) present in the above compound by irradiation of light in the presence of a photosensitizer. Accordingly, the tacky photocurable composition used in this invention does not at all require a volatile crosslinking agent (monomer) such as styrene, is odorless, and has a very fast rate of curing.

The polymer used in the conventional resin-impregnated bandages is highly viscous before impregnation and a volatile crosslinking monomer is required to dilute it. In contrast, in the bandage of this invention, a specific photocurable composition of a relatively low molecular weight is used, and no volatile monomer is required, and moreover, after impregnating the composition in a fabric, it can be cured by polymerization.

The reaction product of components (A), (B) and (C) is prepared in the following manner.

First, at least about 0.55 mole of the diisocyanate (sometimes abbreviated to "D") is added to 1 mole of the hydroxyalkyl acrylate or methacrylate (sometimes abbreviated to "acrylate" or "H") to react the isocyanate groups of the diisocyanate with the hydroxyl group of the acrylate. This reaction affords a mixture of an adduct resulting from the addition of one molecule of the acrylate to one molecule of the isocyanate (sometimes abbreviated to "H.D adduct") and an adduct resulting from the addition of 2 molecules of the acrylate to one molecule of the diisocyanate (sometimes abbreviated to "H.D.H adduct"). After the completion of the reaction of the hydroxyl group of the acrylate with the isocyanate groups of the diisocyanate, the polyhydric alcohol such as a glycol or triol (sometimes abbreviated to "G") is added in an amount such that the amount of hydroxyl groups becomes at least 100 equivalent %, preferably at least 105 equivalent %, of the isocyanate groups remaining in the H.D adduct to complete the reaction of the isocyanate groups of the H.D adduct with the hydroxyl groups of the polyhydric alcohol and to form a product resulting from the addition of one to several molecules of H.D to the polyhydric alcohol, for example, a mixture of the H.D.G adduct and H.D.G.D.H adduct.

In the reaction product of components (A), (B) and (C), the proportions of the H.D. adduct, H.D.G adduct and H.D.G.D.H adduct vary according to the proportions of the acrylate, diisocyanate and polyhydric alcohol to be mixed or reacted, and besides the above adducts, polyadducts such as H.(D.G)$_n$.D.H adduct or H.(D.G)$_n$ adduct also occur. These polyadduct also polymerize upon irradiation of light, and are contained in the cured product as constituent elements. It is essential that the main reaction product of components (A), (B) and (C) in accordance with this invention contain at least one compound having at least two acrylate groups added thereto such as H.D.H or H.D.G.D.H. Since these compounds contain at least two acrylate grups as functional groups, they polymerize and crosslink upon irrdiation of light in the presence of a photosensitizer.

In the present invention, the reaction is carried out in two stages as mentioned above. This is because if the acrylate remains unreacted with the diisocyanate, it gives off an unpleasant odor, and is likely to cause inflammation or blister upon contact with the skin. Thus, it is necessary to react the acrylate completely with the diisocyanate.

In the second stage of the reaction, the polyhydric alcohol is added so that the amount of the hydroxyl groups is in excess of the isocyanate groups remaining in the H.D adduct. This is because of the need to react the isocyanate groups completely so that they do not exist in the free state. When free isocyanate groups remain in the product, the properties of the resin are likely to change with time as a result of water absorption. This can be avoided by reacting the hydroxyl groups in slight excess.

Examples of the hydroxyalkyl acrylate used as component (A) in this invention are 2-hydroxyethyl acrylate, 2-hydroxypropyl acrylate, 2-hydroxyethyl methacrylate, and 2-hydroxypropyl methacrylate. They can be used either alone or in admixture of two or more. Of these, 2-hydroxyethyl acrylate, 2-hydroxypropyl acrylate, 2-hydroxyethyl methacrylate, and mixtures of these are especially preferred.

Examples of the diisocyanate used as component (B) in the present invention include 2,4-toluene diisocyanate, 2,6-toluene diisocyanate, hexamethylene diisocyanate, diphenylmethane diisocyanate, naphthylene diisocyanate, tolidine diisocyanate, and xylylene diisocyanate. They can be used either alone or in admixture of two or more. Of these, 2,4-toluene diisocyanate, 2,6-toluene diisocyanate, hexamethylene diisocyanate, and especially mixtures of these are preferred.

Examples of the polyhydric alcohol as component (C) include ethylene glycol, diethylene glycol, dipropylene glycol, triethylene glycol, tetraethylene glycol, 1,2-propylene glycol, 1,3-propylene glycol, 1,4-butanediol, 1,2-butanediol, 1,6-hexanediol, glycerol, pentaerythritol, trimethylol propane, trimethylol ethane, and cyclohexane dimethanol. Of these, diethylene glycol is especially preferred. They can be used either alone or in combination of two or more.

The proportion of the diisocyanate is 0.55 to 3 moles, preferably 0.7 to 2 moles, per mole of the hydroxyalkyl acrylate, and the proportion of the polyhydric alcohol is such that the proportion of the hydroxyl groups is 1.0 to 2.0 moles, preferably 1.05 to 1.5 moles, based on the remaining isocyanate groups. When the proportion of the diisocyanate is less than 0.55 moles, the hydroxyalkyl acrylate remains unreacted, and is likely to cause an offensive odor. When it is more than 3 moles, the composition after photocuring is so hard as to make it unsuitable for use in the present invention. When the proportion of the hydroxyl groups of the polyhydric alcohol is less than 1.0 molar times the remaining isocyanate groups, the isocyanate groups naturally remain undesirably in the final resin composition. On the other hand, when the proportion of the hydroxyl groups of the polyhydric alcohol exceeds 2.0 molar times the remaining isocyanate groups, the content of photopolymerizable carbon-carbon double bonds decreases excessively and the unreacted polyhydric alcohol remains in a large quantity. Neither of the above-mentioned results are desirable.

The diisocyanate and the polyhydric alcohol can be used, in the form of their reaction product, either wholly or in part. Such a reaction product can be obtained easily in the market. For example, a solution of a reaction product of 1 mole of trimethylol propane and 3 moles of toluene diisocyanate is available frm Bayer AG under the trademark Desmodur L. It can also be synthesized in situ.

Various photosensitizers can be used in the present invention, and examples include benzoin, benzophenone, azobisisobutyronitrile, naphthalenesulfonamide, and benzoin monomethyl ether. The amount of the photosensitizer is 0.002 to 5% by weight, preferably 0.5 to 3% by weight, based on the weight of the photocurable composition used.

The flexible fabric used in this invention may, for example, be woven or non-woven fabrics made of mineral fibers such as glass fibers, animal or plant fibers such as wool, cotton or flax, and synthetic fibers such as polyamides or polyesters. Of these, the use of a flexible base material composed of glass fibers is especially preferred.

The production of the storage-stable, flexible photocurable orthopedic material fabrics of this invention will be described below.

The orthopedic material of this invention can be produced mainly by the following two methods.

One method comprises impregnating the flexible fabric with a tacky composition comprising a reaction product of components (A), (B) and (C) during the preparation of this composition. Specifically, it comprises (1) a first step of reacting the acrylate with 0.55 to 3 moles, per mole of the acrylate, of diisocyanate to form a reaction product in which free isocyanate groups remain, (2) a second step of adding the polyhydric alcohol to the reaction product of the first step to form a reactive composition, (3) a third step of impregnating the resulting reactive composition in the flexible fabric in the absence of a solvent, (4) adding the photosensitizer in the first, second or third step, and (5) a fourth step of completing the reaction of the free isocyanate groups and the polyhydric alcohol in the impregnated composition.

According to this method, the reactive composition obtained through the first and second step it is itself a low viscosity liquid having a viscosity of 5 to 30 poises, preferably 10 to 20 poises, suitable for impregnation in the fabric. After impregnation, the reaction can be performed so as to convert it to a non-flowable and tacky composition convenient for handling the impregnated fabric, for example, for applying to a body member. No solvent is used in this method, and therefore, no step is required to remove the solvent. The orthopedic material in accordance with this invention can thus be produced very advantageously.

It is important in this method that the flexible fabric should be impregnted with the reactive composition prepared in the second step at an initial stage of the reaction of the isocyanate groups remaining in the reactive composition with the hydroxyl groups of the polyhydric alcohol, and after impregnation, the above reaction is completed to consume free isocyanate groups substantially. The above reaction can be completed by allowing the fabric impregnated with the reactive composition to stand for several to several tens of days at a temperature ranging from room temperature to about 40° C. in a light-shielded sealed condition.

The flexible fabric is impregnated with the reactive composition by dipping the fabric in a bath containing the reactive composition and the photosensitizer, pulling it up from the bath, and squeezing it by, for example, rolls. Alternatively, the reactive composition may be coated on the fabric.

When the impregnation of the fabric is carried out continuously, the reactive composition immediately after the addition of the polyhydric alcohol is fed into the bath intermittently or continuously during the impregnation of the fabric so that an increase in the viscosity of the reactive composition will not cause difficulties in the impregnation of the fabric.

The other method comprises impregnating the flexible fabric with the tacky composition obtained by complete reaction of the components (A), (B) and (C), in the presence of a solvent, and then volatilizing the solvent. Specifically, it involves (1) a first step of reacting the acrylate with 0.55 to 3 moles, per mole of the acrylate, of the diisocyanate to form a reaction product in which free isocyanate groups remain, (2) a second step of reacting the reaction product of the first step with the polyhydric alcohol to form a reaction product containing substantially no free isocyanate groups, (3) a third step of impregnating the flexible fabric with a solution of the reaction product of the second step, (4) adding the photosensitizer and a solvent inert to the isocyanate groups either in the first, second or third step, and (5) a fourth step of volatilizing the solvent from the impregnated solution.

The solvent used in this method is inert to the isocyanate groups and has the property of dissolving the above reaction product. Examples are dichloromethane, diethyl ether, acetone, chloroform, dioxane, and ethyl acetate.

The amount of the solvent is preferably adjusted to a minimum amount which causes the dissolution of the reaction product and makes it easy to impregnate it in the flexible fabric. In the first and/or second step, the reaction can be accelerated by adding a urethanization catalyst (for example, dibutyltin laurate, stannous octoate, N-methyl morpholine, N,N-dimethyl cyclohexylamine, or an organic acid salt of 1,8-diazabicyclo (5,4,0)undecene-7 in an amount of 0.0001 to 1 equivalent % based on the isocyanate groups.

According to another method, the tacky composition obtained by reacting the components (A), (B) and (C) is diluted to a preferred viscosity with a solvent, and then impregnated in the fabric. In this method, too, it is very easy to volatilize the solvent alone after impregnation. There is no likelihood of change in the chemical composition of the tacky composition.

In any of the methods described above, the amount of the tacky composition impregnated in the fbric is 25 to 50%, preferably 30 to 45%, based on the total weight of the fabric and the composition.

The orthopedic material so obtained is applied to members of a body in the same way as in the case of known impregnated bandage of the photocurable type containing an unsaturated polyester resin, and is photocured. Specifically, when the orthopedic material of this invention is applied to the site of bone fracture, for example, and exposed to light from an ultraviolet lamp or sunlight lamp, it is easily cured. Suitable light sources are those which emit great quantities of light of long wavelength regions, for example, 3500 to 3800 A. Desirably, the amount of the photosensitizer is adjusted so that the composition can be cured completely by exposure for about 3 to 10 minutes.

The orthopedic material in accordance with this invention can be used not only as bandages but also as splints.

The following Examples illustrate the present invention.

In these examples, all parts and percentages are by weight unless otherwise specified.

The various properties shown in the examples were measured by the following methods.

Thickness of the cured bandage
 Measured by a slide caliper.
Weight proportion of the fabric
 A sample is calcined in an electric oven at 480° C., and the weight residue (%) is determined.
Weitht proportion of the cured composition
 Parts by weight per 100 parts by weight of the bandage.
Flexural rigidity of the cured bandage
 Measured in accordance with ASTM D-747 by bending a specimen 10° an Olsen-type flextural tester.
Viscosity
 Measured by EMILA ROTARY VISCOMETER (a product of Reciprotor A/S, Denmark).

EXAMPLE 1 (PREPARATION OF TACKY COMPOSITION FOR IMPREGNATION)

Four tacky compositions, Acrylate Urethane A, Acrylate Urethane B, Acrylate Urethane C, and Acrylate Urethane D, were prepared in the following manner.

Acrylate Urethane A

A reactor equipped with a stirrer, a water bath for heating and cooling, a temperature controller and a reflux condenser was charged with 34.8 parts (2 moles) of toluene diisocyanate (2,4-:2.6-=80:20) and 23.2 parts (2 moles) of hydroxyethyl acrylate, and they were reacted for 3 hours at 30° C. Furthermore, 0.35 parts of dibutyltin laurate was added as a urethanization catalyst, and the reaction was performed for 1 hour at this temperature.

Then, 11.1 parts (0.15 moles) of diethylene glycol and 69.4 parts of dichloromethane were added to the reaction product, and the mixture was reacted for 6 hours at 45° C. Then, the reaction mixture was cooled down to 20° C., and 2.8 parts of benzophenone was added. The product was stored in a brown receptacle for use in impregnation. This composition was designated as Acrylate Urethane A.

Acrylate Urethane B

The same procedure as in the preparation of Acrylate Urethane A was repeated except that 26.0 parts (2 moles) of hydroxyethyl methacrylate was used instead of the hydroxyethyl acrylate and the amount of dichloromethane and benzophenone were changed to 72.2 parts and 2.9 parts, respectively. The resulting composition was designates as Acrylate Urethane B.

Acrylate Urethane C

The same procedure as in the preparation of Acrylate Urethane A was repeated except that 8.0 parts (1.05 moles) of 1,2-propylene glycol was used instead of the diethylene glycol, and the amounts of dichloromethane and benzophenone were changed to 66.3 parts and 2.7 parts respectively. The resulting composition was designated as Acrylate Urethane C.

Acrylate Urethane D

The same procedure as in the preparation of Acrylate Urethane A was repeated except that 11.6 parts (1 mole) of hydroxyacrylate and 13.0 parts (1 mole) of hydroxyethyl methacrylate were used instead of 23.2 parts of the hydroxyethyl acrylate and 70.8 parts of diethyl ether was used instead of the dichloromethane. The resulting composition was designated as Acrylate Urethane D.

The infrared absorption spectrum of each of these compositions contained no characteristic absorption band (2280 cm$^{-1}$) ascribable to isocyanate groups, and this led to the confirmation that these Acrylate Urethanes A to D do not contain free isocyanate groups.

EXAMPLE 2

Acrylate Urethane A was impregnated in a glass cloth tape (WF-300 5N, a product of Nitto Spinning Co., Ltd.) in a darkroom, and placed in a brown desiccator. The dichloromethane solvent was removed by reducing the pressure in the desiccator for 30 minutes using an aspirator. Then, the Acrylate Urethane A was cured by exposing the impregnated tape for 3 minutes using an ultraviolet irradiation device (PLANO PS PRINTER A3, a product of Fuji Photographic Film Co., Ltd.) to form a cured tape having high rigidity and the following properties.

Before curing, the impregnated tape (bandage) was soft and tacky, and even when it was allowed to stand indoors for more than 30 minutes, a weight loss upon drying was less than 0.5% and it was substantially odorless.

Thickness: 0.368 mm
Weight proportion of the fabric: 69%
Weight proportion of the cured composition: 31%
Flexural rigidity: 7100 Kg/cm$^2$

EXAMPLE 3 (composition)

The same glass tape as used in Example 2 was impregnated with Rigolac 150 HR (an alkyd-styrene unsaturated polyester resin of the isophthalic acid type with a styrene content of 30%, a product of Showa Kobunshi Kogyo Co., Ltd.) and allowed to stand indoors at 25° C. After a lapse of 30 minutes, the weight loss was 8.5%, and 26% of the styrene contained was lost. At this time, an unpleasant odor of the styrene filled the room.

EXAMPLE 4

The procedure of Example 2 was repeated except that a mesh leno-weave glass cloth tape (WG 310, a product of Nito Spinning Co., Ltd., calcined for 8 hours at 450° C.) was used instead of the glass cloth tape in order to improve its air-permeability. A cured tape having the following properties was obtained.

Thickness: 1.10 mm
Weight proportion of the fabric: 62%
Weight proportion of the cured composition: 38%
Flexural rigidity: 1400 Kg/cm$^2$

EXAMPLE 5

The same procedure as in Example 2 was repeated except that a polypropylene woven cloth tape (Yuka Cross Sheet, a product of Mitsubishi Petrochemical Co., Ltd.) was used instead of the glass cloth tape. The resulting cured tape had the following properties.

Thickness: 1.0 mm
Flexural rigidity: 1600 Kg/cm$^2$

EXAMPLES 6 to 9

A cylindrical structure made of paperboard with a diameter of 8 cm and a length of 30 cm was covered with a polyethylene film. A bandage with a width of 6 cm was prepared by impregnating the same mesh leno-weave glass cloth tape as used in Example 4 with each of the Acrylate Urethanes A to D and then drying it. The bandage was wrapped around the polyethylene film-covered cylindrical structure, and the entire surface of the wrapped bandage was exposed to light from a sunlight lamp placed about 20 cm from it for an average of 3 minutes to cure the tacky composition in the bandage. After removal of the cylinder, all of the cured bandages were light in weight and had high rigidity and toughness.

EXAMPLE 10

23.2 Parts (2 moles) of hydroxyethyl acrylate and 34.8 parts (2 moles) of toluene diisocyanate (2,4-:2,6-=80:20) were reacted for 8 hours at 40° to 50° C., and then cooled. Then, 11.1 parts (1.05 moles) of diethylene glycol and 2.7 parts of benzophenone were added (no solvent was added) to form a reactive composition. The reactive composition was immediately impregnated in the same glass cloth tape as used in Example 4, and the impregnated cloth tape was placed in a black polyethylene bag and allowed to stand for 2 weeks at room temperature. A small amount of the tacky composition was plucked off from the surface of the resulting photo-curable bandage, and analyzed by infrared absorption spectroscopy. No free isocyanate group was detected.

The photocurable bandage was cured in the same way as in Examples 6 to 9. Almost the same results as in Examples 6 to 9 were obtained.

EXAMPLE 11

29.0 Parts (2.5 moles) of hydroxyethyl acrylate, 34.8 parts (2 moles) of tolylene diisocyanate (2,4-:2,6-=80:20), and 2.2 parts of benzoin methyl ether were reacted for 5 hours at 45° to 50° C. in a light-shielded condition, and the product was allowed to stand at room temperature for 2 days in a sealed air in the absence of light. Then, 10.6 parts (1 mole) of diethylene glycol was added at room temperature, and the mixture was immediately impregnated in a glass cloth tape (WF-300 5N, a product of Nitto Spinning Co., Ltd.) in a darkroom. The impregnated glass tape was placed in a brown glass bottle, and allowed to stand at room temperature for 1 week. It was ascertained that no free isocyanate group was present. The impregnated tape was cured by exposure of ultraviolet rays for 4 minutes in the same way as in Example 2. The resulting cured tape had the following properties.

Thickness: 0.43 mm
Weight proportion of the fabric: 55%
Weight proportion of the cured composition: 45%
Flexural rigidity: 6400 Kg/cm$^2$

EXAMPLE 12

32.5 parts (2.5 moles) of hydroxyethyl methacrylte, 34.8 parts (2 moles) of toluene diisocyanate (2,4-:2,6-=80:20) and 2.4 parts of benzoin methyl ether were reacted at 70° C. for 4 hours, and allowed to stand for 2 days at room temperature in a sealed air in the absence of light to afford a white solid product. The product was melted by heating it to 70° C., and immediately then, 10.6 parts (1 mole) of diethylene glycol was added to form a liquid reactive composition. It was impregnated in the same way as in Example 11, and the impregnated tape having the following properties.

Thickness: 0.35 mm
Weight proportion of the fabric: 66%
Weight proportion of the cured composition: 34%
Flexural rigidity: 8800 Kg/cm$^2$

EXAMPLE 13

The same procedure as in Example 11 was repeated except that the amounts of the hydroxyethyl acrylate benzoin methyl ether and diethylene glycol were changed to 23.2 parts (2 moles), 2.1 parts, and 12.3 parts (1.16 moles), respectively. The resulting cured tape had the following properties.

Thickness: 0.36 mm
Weight proportion of the fabric: 65%
Weight proportion of the cured composition: 35%
Flexural rigidity: 5100 Kg/cm$^2$

EXAMPLE 14

A person was bandaged at his elbow using a speed bandage (TE 1802-2, a product of Tokyo Eizai Lab. Co., Ltd.), and the bandage obtained in Example 4 was wrapped on it. It was cured by exposure to a sunlight lamp placed about 20 cm away from it. During this time, neither the bandaged person nor a person who applied the bandage smelt an offensive smell. The cured bandage fixed the elbow firmly. Hence, it was confirmed that the bandage could be used with good results as an orthopedic bandage.

EXAMPLE 15

11.6 Parts (1 mole) of hydroxyethyl acrylate, 19.5 parts (1.5 moles) of hydroxyethyl methacrylate, 26.1 parts (1.5 moles) of toluene diisocyanate (2,4-:2,6-=80:20) and 8.4 parts (0.5 mole) of hexamethylene diisocyanate were reacted for 4 hours at 70° C., and cooled. The conversion of the hydroxyalkyl acrylate at this time was found to be 99% as a result of the determination of the amount of residual isocyanate groups.

Then, 10.6 parts (1 mole) of diethylene glycol and 2.3 parts of benzoin methyl ether were added to the reaction product. The resulting composition had a viscosity of 6 poises. The composition was rapidly impregnated in a lenoweave glass tape (5 mesh, 10 cm wide, 36 g per meter, a product of Arisawa Seisakusho Co., Ltd.). The resulting impregnated bandage was placed on a polyethylene film, wound up, and filled in a black polyethylene bag in the same way as in Example 10. It was stored in a darkroom. Two weeks later, the impregnated glass tape was taken out, and wrapped in three layers around a polyvinyl chloride resin pipe, 75 mm in diameter, covered with a polyethylene film. It was then cured by exposing it for 1 to 4 minutes using a cylindrical irradiation device in which twenty 20W fluorescent lamps for hotochemistry were arranged so that the inside diameter of the cylinder became 40 cm.

The cured product was removed frm the polyvinyl hloride resin pipe, and its weight was found to be 60 g. Then, its flattening compression strength (rate of distortion 10%) was measured using a tensile tester (Autograph IS-500, a product of Shimazu Seisakusho Co., Ltd.). The results were as follows:

| | |
|---|---|
| After exposure for 1 minute | 26 Kg |
| After exposure for 2 minutes | 31 Kg |
| After exposure for 3 minutes | 38 Kg |
| After exposure for 4 minutes | 41 Kg |
| After exposure for 4 minutes and then standing for 24 hours | 43 Kg |
| After exposure for 4 minutes and then standing for 48 hours | 45 Kg |

After use, the cured bandage could be easily stripped off by pulling its end by hand.

When the photocurable bandage was used after storage in a black polyethylene film bag for 6 months its trength was almost the same as above.

EXAMPLE 16 (comparison)

The same glass tape as used in Example 15 was impregnated with an unsaturated polyester resin containng 3 wt% of benzoin methylester curable in air (Rigoac 158 BQT, a product of Showa Kobunshi Kogyo Co., Ltd.) (the resin content in the impregnated tape being 10%). Immediately then, it was wound up on a polyvinyl chloride resin pipe, and cured by exposure. Its flattening compression strength was as follows:

| | |
|---|---|
| After exposure for 2 minutes | 1 Kg |
| After exposure for 4 minutes | 10 Kg |
| After exposure for 8 minutes | 23 Kg |
| After exposure for 16 minutes | 35 Kg |
| After exposure for 32 minutes | 45 Kg |

When it was allowed to stand for 2 days after exposure for 32 minutes, the offensive smell of styrene did not go off.

After use, the cured bandage could not be stripped off by hand, but could be removed only by using a plaster saw.

EXAMPLE 17 (comparison)

A bandage impregnted with calcined gypsum (PLAS RUN-Gyps. T-1083, a product of Tokyo Eizai Lab. Co., Ltd.), 10 cm wide, was wrapped in 10 layers, and dried for 2 days. Its weight was 120 g. It was found to have a flattening compression strength of 30 Kg by the same method as in Example 15.

What we claim is:

1. A storage-stable flexible photocurable orthopedic material such as bandage or splint for application to a body member, said orthopedic material comprising a flexible fabric, a photosensitizer and a photocurable tacky composition impregnated in the fabric, said tacky composition being a reaction product obtained by reacting a reaction product (D) of
    A. at least one hydroxyalkyl acrylate or hydroxyalkyl methacrylate, wherein said hydroxyalkyl portion contains 2 or 3 atoms and
    B. 0.55 to 3 moles, per mole of said acrylate, of at least one diisocyanate of the following formula

OCN—R₁—NCO wherein R₁ represents $-(CH_2)_6$,

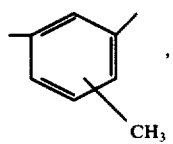

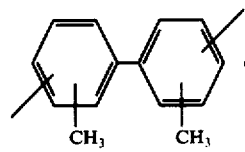

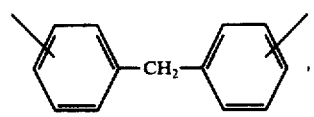

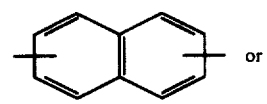 or

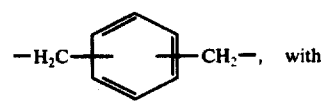, with

C. at least one polyhydric alcohol of the following formula $R_2(OOH)_m$ wherein $R_2$ represents a straight-chain or branched chain saturated aliphatic hydrocarbon group containing 2 to 8 carbon atoms, a cycloaliphatic hydrocarbon group, or the group

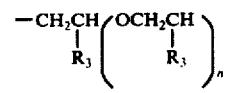

in which n is a number of 1 to 4 and $R_3$ is a hydrocarbon atom or a methyl group, and m is 2,
    wherein the amount of the polyhydric alcohol (C) is one which affords 1.05 to 1.50 equivalents, of hydroxyl groups based on the isocyanate groups remaining in the reaction product (D),
said reaction product of (D) and (C) containing at least one compound having at least two carbon-carbon double bonds capable of being polymerized and crosslinked by light and being substantially free from free isocyanate groups.

2. The orthopedic material of claim 1 wherein the hydroxyalkyl acrylate or hydroxyalkyl methacrylate as component (A) is at least one member selected from the group consisting of 2-hydroxyethyl acrylate, 2-hydroxypropyl acrylate, 2-hydroxyethyl methacrylate and 2-hydroxypropyl methacrylate.

3. The orthopedic material of claim 1 wherein the diisocyanate as component (B) is at least one member selected frm the group consisting of 2,4-toluene diisocyanate, 2,6-toluene diisocyanate, and hexamethylene diisocyanate.

4. The orthopedic material of claim 1 wherein the polyhydric alcohol as component (C) is at least one member selected from the group consisting of diethylene glycol, dipropylene glycol, tetraethylene glycol, 1,2-propylene glycol, 1,4-butanediol and 1,6-hexanediol.

5. A method for producing a storage-stable flexible photocurable orthopedic material such as a bandage or splint for application to a body member, comprising a flexible fabric, a photosensitizer and a photocurable tacky composition containing at least one compound containing at least two carbon-carbon double bonds capable of being polymerized and crosslinked by light and being substantially free from free isocyanate groups, said method comprising the steps of:

1. a first step of reacting (A) at least one hydroxyalkyl acrylate or hydroxyalkyl methacrylate wherein said hydroxyalkyl portion contains 2 or 3 carbon atoms, with (B) 0.55 to 3 moles, per mole of the hydroxyalkyl acrylate or hydroxyalkyl methacrylate, of at least one diisocyanate of the formula

OCN—R₁—NCO wherein R₁ is 

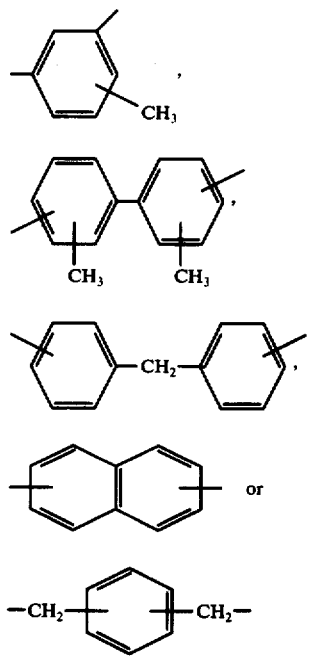

to form a reaction product (D) containing remaining free isocyanate groups, 2. a second step of adding (C) at least one polyhydric alcohol of the following formula

R₂(OH)ₘ wherein R₂ represents a straight-chain or branched chain aliphatic hydrocarbon group containing 2 to 8 carbon atoms, a cycloaliphatic hydrocarbon group or the group

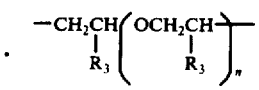

in which n is a number of 1 to 4, and R₃ is a hydrogen atom or a methyl group, and m is 2, wherein the amount of the polyhydric alcohol (C) is one which affords 1.05 to 1.5 equivalents, of hydroxyl groups based on the remaining isocyanate groups in the reaction product (D) of the first step, to form a reactive composition, 3. a third step of impregnating the flexible fabric with the reactive composition in the absence of a solvent,
4. adding photosensitizer either in the first, second or third step, and
5. a fourth step of completing the reacton of the free isocyanate groups in the impregnated composition with the polyhydric alcohol (C).

6. The method of claim 5 wherein said reactive composition is impregnated in the flexible fabric while it has a viscosity of 5 to 30 poises.

7. The method of claim 5 wherein the hydroxyalkyl acrylate or hydroxyalkyl methacrylate (A) is at least one member selected from the group consisting of 2-hydroxyethyl acrylate, 2-hydroxypropyl acrylate, 2-hydroxyethyl methacrylate and 2-hydroxypropyl methacrylate.

8. The method of claim 5 wherein the diisocyanate (B) is at least one member selected from the group consisting of 2,4-toluene diisocyanate, 2,6-toluene diisocyanate, and hexamethylene diisocyanate.

9. The method of claim 5 wherein the polyhydric alcohol (C) is at least one member selected from the group consisting of diethylene glycol, dipropylene glycol, tetraethylene glycol, 1,2-propylene glycol, 1,4-butanediol and 1,6-hexanediol.

10. A method for producing a storage-stable flexible photocurable orthopedic material such as a bandage or splint for application to a body member, comprising a flexible fabric, a photosensitizer and a photocurable tacky composition containing at least one compound containing at least two carbon-carbon double bonds capable of being polymerized and crosslinked by light and being substantially free from free isocyanate groups, said method comprising the steps of:

1. a first step of reacting (A) at least one hydroxyalkyl acrylate or hydroxyalkyl methacrylate wherein said hydroxyalkyl portion contains 2 or 3 carbon atoms with (B) 0.55 to 3 moles, per mole of the hydroxyalkyl acrylate or methacrylate, of at least one diisocyanate of the formula

OCN—R₁—NCO wherein R₁ represents 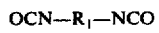

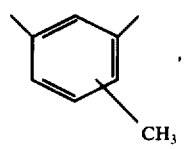

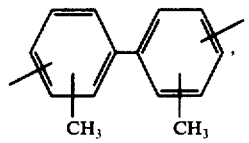

-continued

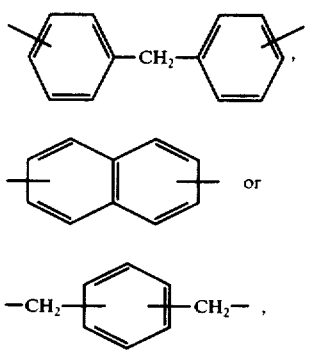

to form a reaction product (D) containing remaining free isocyanate groups, 2. a second step of adding (C) at least one polyhydric alcohol of the following formula

$R_2(OH)_m$ wherein $R_2$ represents a straight-chain or branched chain aliphatic hydrocarbon group containing 2 to 8 carbon atoms, a cycloaliphatic hydrocarbon group, or the group

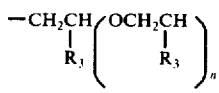

$$-CH_2CH\left(\begin{matrix} OCH_2CH \\ | \\ R_3 \end{matrix}\right)_n$$
$$\phantom{-CH_2CH}|\phantom{\left(\begin{matrix}OCH_2CH\\|\\R_3\end{matrix}\right)_n}$$
$$\phantom{-CH_2CH}R_3$$

in which $n$ is a number of 1 to 4 and $R_3$ is a hydrogen atom or a methyl group, and $m$ is 2, wherein the amount of the polyhydric alcohol is one which affords 1.05 to 1.5 equivalents, of hydroxyl groups based on the isocyanate groups remaining in the reaction product (D) of the first step, to form a reaction product (D) containing substantially no free isocyanate groups, 3. a third step of impregnating the flexible fabric with a solution of the reaction product of the second step,
4. adding a photosensitizer and a solvent inert to the isocyanate groups either in the first, second or third step, and
5. volatilizing the solvent form the impregnated solution.

11. The method of claim 10 wherein the reaction in the first and/or second step is carried out in the presence of a urethanization catalyst.

12. The method of claim 10 wherein the hydroxyalkyl acrylate or hydroxyalkyl methacrylate (A) is at least one member selected from the group consisting of 2-hydroxyethyl acrylate, 2-hydroxypropyl acrylate, 2-hydroxyethyl methacrylate and 2-hydroxypropyl methacrylate.

13. The method of claim 10 wherein the diisocyanate (V) is at least one member selected from the group consisting of 2,4-toluene diisocyanate, 2,6-toluene diisocyanate, and hexamethylene diisocyanate.

14. The method of claim 10 wherein the polyhydric alcohol (C) is at least one member selected from the group consisting of diethylene glycol, dipropylene glycol, tetraethylene glycol, 1,2-propylene glycol, 1,4-butanediol and 1,6-hexanediol.

15. The orthopedic material of claim 1 wherein the hydroxyalkyl acrylate or hydroxyalkyl methacrylate (A) is at least one member selected from the group consisting of 2-hydroxyethyl acrylate, 2-hydroxypropyl acrylate and 2-hydroxyethyl methacrylate; said diisocyanate (B) is at least one member selected from the group consisting of 2,4-toluene diisocyanate, 2,6-toluene diisocyanate and hexamethylene diisocyanate; and the polyhydric alcohol (C) is at least one member selected from the group consisting of diethylene glycol, dipropylene glycol, tetraethylene glycol, 1,2-propylene glycol, 1,4-butanediol and 1,6-hexanediol.

16. The method of claim 5 wherein the hydroxyalkyl acrylate or hydroxyalkyl methacrylate (A) is at least one member selected from the group consisting of 2-hydroxyethyl acrylate, 2-hydroxypropyl acrylate and 2-hydroxyethyl methacrylate; said diisocyanate (B) is at least one member selected from the group consisting of 2,4-toluene diisocyanate, 2,6-toluene diisocyanate and hexamethylene diisocyanate; and the polyhydric alcohol (C) is at least one member selected from the group consisting of diethylene glycol, dipropylene glycol, tetraethylene glycol, 1,2-propylene glycol, 1,4-butanediol and 1,6-hexanediol.

17. The method of claim 10 wherein the hydroxyalkyl acrylate or hydroxyalkyl methacrylate (A) is at least one member selected from the group consisting of 2-hydroxyethyl acrylate, 2-hydroxypropyl acrylate and 2-hydroxyethyl methacrylate; said diisocyanate (B) is at least one member selected from the group consisting of 2,4-toluene diisocyanate, 2,6-toluene diisocyanate and hexamethylene diisocyanate; and the polyhydric alcohol (C) is at least one member selected from the group consisting of diethylene glycol, dipropylene glycol, tetraethylene glycol, 1,2-propylene glycol, 1,4-butanediol and 1,6-hexanediol.

* * * * *